US012736512B2

(12) United States Patent
Çubukçu

(10) Patent No.: US 12,736,512 B2
(45) Date of Patent: Sep. 15, 2026

(54) IN-TANK RAW MILK MONITORING SYSTEM AND METHOD

(71) Applicant: Rawbox Teknoloji A.Ş., Kocaeli (TR)

(72) Inventor: Nüzhet Emir Çubukçu, Kocaeli (TR)

(73) Assignee: Rawbox Teknoloji A.S., Kocaeli (TR)

( * ) Notice: Subject to any disclaimer, the term of this patent is extended or adjusted under 35 U.S.C. 154(b) by 359 days.

(21) Appl. No.: 18/568,808

(22) PCT Filed: Feb. 9, 2023

(86) PCT No.: PCT/TR2023/050119
§ 371 (c)(1),
(2) Date: Dec. 9, 2023

(87) PCT Pub. No.: WO2024/151231
PCT Pub. Date: Jul. 18, 2024

(65) Prior Publication Data

US 2025/0231164 A1 Jul. 17, 2025

(30) Foreign Application Priority Data

Jan. 13, 2023 (TR) ................................ 2023/000448

(51) Int. Cl.

| | |
|---|---|
| ***G01N 33/04*** | (2006.01) |
| ***A01J 5/007*** | (2006.01) |
| ***A01J 9/00*** | (2006.01) |
| ***G01N 33/14*** | (2006.01) |
| ***G06Q 10/08*** | (2023.01) |
| ***H04W 4/38*** | (2018.01) |
| *A01J 9/04* | (2006.01) |
| *G06Q 50/02* | (2012.01) |

(52) U.S. Cl.
CPC .............. *G01N 33/04* (2013.01); *A01J 5/007* (2013.01); *A01J 9/00* (2013.01); *G01N 33/14* (2013.01); *G06Q 10/08* (2013.01); *H04W 4/38* (2018.02); *A01J 9/04* (2013.01); *G06Q 50/02* (2013.01)

(58) Field of Classification Search
CPC .... A01J 5/007; A01J 7/022; A01J 9/00; A01J 9/04; G01N 33/04; H04W 4/38; G06Q 50/02
See application file for complete search history.

(56) References Cited

U.S. PATENT DOCUMENTS

| | | | | |
|---|---|---|---|---|
| 2021/0176950 | A1 | 6/2021 | Jensen | |
| 2022/0268620 | A1 | 8/2022 | Schiller | |
| 2023/0329185 | A1* | 10/2023 | Lax | A61L 2/18 |

FOREIGN PATENT DOCUMENTS

| | | | | |
|---|---|---|---|---|
| CN | 107481159 | A * | 12/2017 | A01K 29/005 |
| DE | 102009009552 | A1 * | 9/2010 | A01J 5/045 |
| DE | 202020000234 | U1 * | 3/2020 | G06Q 50/02 |
| EP | 3854205 | A1 | 7/2021 | |
| WO | WO-02074069 | A1 * | 9/2002 | A01J 5/0175 |
| WO | WO-2016162654 | A1 * | 10/2016 | A01J 5/007 |
| WO | 2021001378 | A1 | 1/2021 | |

OTHER PUBLICATIONS

Çubukçu, N., PCT/TR2023/050119, International Search Report, Oct. 10, 2023, 3 pages.
Çubukçu, N., PCT/TR2023/050119, Written Opinion, Oct. 10, 2023, 3 pages.
Karras, A., "SAF: The Design of a P2P-IoT Lo Ra System for Smart Agriculture Supply Chains," 18th International Conference on Artificial Intelligence Applications and Innovations (AIAI 2022), Hersonissos, Crete, Greece, Jun. 17-20, 2022, 12 pages.
Gehlot, A., "Dairy 4.0: Intelligent Communication Ecosystem for the Cattle Animal Welfare with Blockchain and IoT Enabled Technologies," Appl. Sci. 2022, 12, 7316, 19 pages.
Çubukçu, N., 23808647.4-1001, European Search Report, Oct. 2, 2025, 9 pages.

* cited by examiner

*Primary Examiner* — Benjamin R Schmitt
(74) *Attorney, Agent, or Firm* — Rahman LLC

(57) ABSTRACT

The invention relates to an in-tank raw milk monitoring system and method used in the agriculture and animal husbandry sector, in the field of food production, especially in the cooling and storage tanks in raw milk collection centers, which allows remote and digital measurement of milk quality determining values such as temperature and pH and milk quantity, storage and transmission of these measurement values to remote computers, remote and real-time 24/7 monitoring of tanks, and all these operations to be carried out with minimal need for personnel intervention, which is compatible with industrial computer systems and cloud systems, sends mobile sms and e-mail notifications, can be managed by artificial intelligence thanks to the software it contains, creates a suitable ground for data mining and reporting, and saves labor, energy and time accordingly.

2 Claims, No Drawings

IN-TANK RAW MILK MONITORING SYSTEM AND METHOD

TECHNICAL FIELD

The invention relates to an in-tank raw milk monitoring system and method used in the agriculture and animal husbandry sector, in the field of food production, especially in the cooling and storage tanks in raw milk collection centers, which allows remote and digital measurement of milk quality determining values such as temperature and pH and milk quantity, storage and transmission of these measurement values to remote computers, remote and real-time 24/7 monitoring of tanks, and all these operations to be carried out with minimal need for personnel intervention, which is compatible with industrial computer systems and cloud systems, sends mobile sms and e-mail notifications, can be managed by artificial intelligence thanks to the software it contains, creates a suitable ground for data mining and reporting, and saves labor, energy and time accordingly.

PRIOR ART

One of the most important criteria determining the quality of raw milk is the pH value of the milk, which should be in a sensitive range of 6.5 to 6.7. The staff of milk producer companies go to milk collection centers, measure the pH value of milk in milk storage and cooling tanks with handheld devices, logistics production planning of milk is made according to these values, and milk of insufficient quality is not purchased and no shipped to the factory. These current methods have many disadvantages. Namely, pH data of milk cannot be measured digitally, There are between 3000 and 5000 milk collection centers all over Turkey and it is not possible to send personnel to each center and make quality control measurements, Since the quality controls of raw milk cannot be carried out on site, that is, in collection centers, these control procedures can be carried out after the milk is shipped to the factory and before the milk enters into production process, and raw milk that does not meet quality standards is not accepted by the factory and is disposed of, As a result of this process, farmers and producers suffer financial losses, and ecological damage occurs with inefficient animal husbandry, inefficient logistics and increased carbon footprint.

Although the raw milk cooling and storage tanks currently in use have the ability to digitally measure the quantity and temperature of milk, these tanks cannot measure the pH value, which is one of the most important criteria affecting milk quality. For this reason, the personnel going to milk collection centers should perform this process with handheld terminals.

There are some studies for raw milk quality and control analysis and a national patent application no. TR2022/000199 mentions a study on "Milk analysis, collection and processing system". Described herein is a milk analysis, collection and processing system that enables the analysis of the nutritional values of the milk, keeping records of the analysis values obtained, collecting statistical and financial data with the recorded data, and instant monitoring of the status of the collected milk at the moment of receipt of the milk from the producer during the raw milk collection process in dairy and/or milk and dairy products production sectors.

When the above-mentioned patent document is examined, it is seen that the milk quality is determined by the personnel going to the milk collection centers using handheld devices and the data obtained are entered into the system by the personnel using handheld terminals. The document does not mention any structure that minimizes personnel intervention, performs automatic monitoring and measurement remotely and in real time, and automatically stores and shares data with remote centers. This shows that the system described in the relevant document cannot solve the problems mentioned above.

Thus, the need to eliminate such shortcomings and disadvantages of the embodiments and practices employed in the prior art entails an improvement in the respective technical field.

DESCRIPTION OF THE INVENTION

The present disclosure relates to an in-tank raw milk monitoring system and method developed for eliminating the aforementioned disadvantages and providing new advantages to the respective technical field.

The aim of the invention is to provide an embodiment designed to be used in the agriculture and animal husbandry sector, in the field of food production, especially in the cooling tanks located in raw milk collection centers, allowing remote and digital measurement of milk quality determining values such as temperature and pH and milk quantity, storage and transmission of these measurement values to remote centers, remote and real-time 24/7 monitoring of the tanks and all these operations to be carried out with minimal need for personnel intervention.

Another aim of the invention is to provide an embodiment that is compatible with industrial computer systems and cloud systems, sends mobile sms and e-mail notifications, and provides a suitable basis for data mining and reporting.

Another aim of the invention is to provide an embodiment that saves labor, energy and time, prevents financial losses of farmers and producers, makes it possible for animal husbandry and logistics activities to achieve an efficient quality, and minimizes ecological damage by reducing carbon footprint.

The structural and characteristic features of the present disclosure, including all of its advantages, will be more clearly understood when the detailed description given below is read, and thus, the present disclosure should be evaluated by taking this detailed description into consideration.

DETAILED DESCRIPTION OF THE INVENTION

The invention relates to an in-tank raw milk monitoring system and method used in the agriculture and animal husbandry sector, in the field of food production, especially in the cooling and storage tanks in raw milk collection centers, which allows remote and digital measurement of milk quality determining values such as temperature and pH and milk quantity, storage and transmission of these measurement values to remote computers, remote and real-time 24/7 monitoring of tanks, and all these operations to be carried out with minimal need for personnel intervention, which is compatible with industrial computer systems and cloud systems, sends mobile sms and e-mail notifications, can be managed by artificial intelligence thanks to the software it contains, creates a suitable ground for data mining and reporting, and saves labor, energy and time accordingly.

The invention comprises a system comprising hardware mounted on a raw milk cooling and storage tank and a software embedded in the hardware, and a method of operation of the system.

There are two requirements for measuring the pH value. One is to keep the pH sensor bar in a protective solution and the other is to calibrate the probe before measurements. The invention enables these two actions to be performed automatically, minimizing human intervention. With the sensors in the box mounted on the tank in which the milk is stored, all processes of the tank can be informed and the tank can be monitored remotely. Depending on the time when pH measurement is required, the pH probe automatically contacts the milk or the probe is kept in a protective solution.

The inventive system is generally composed of 12V transformer to create a direct current source for different units, Lora terminal, LTE and Lora antenna to provide wireless long distance data exchange, liquid level sensor to measure the amount of liquid coming into the sample container, pressure sensor to measure the liquid pressure in the tank, peristaltic pump to provide liquid flows, manual valve for solution filling and draining, LCD monitor for on-screen monitoring and management, pH sensor for pH determination of milk, LTE modem for mobile network connectivity, first microcomputer for data processing and management, second microcomputer for data acquisition and sensor management, Lora Gateway to collect wireless and long-distance sensor data, voltage regulator to supply different voltage values to components, temperature sensor to measure tank temperature, relay board and relay driver board to manage valves and pumps, solenoid valve to connect the sample container to the tank, the solution box for sample and solution discharge, UART card for communication between the microcomputer and the relay driver card, float to measure the full and empty status of the solution containers, UPS to provide uninterrupted power to the system, sensor circuit to perform sensor data calculation and adjustment operations.

The inventive system operates as described below.

In General

The first microcomputer connects to the cloud via the mobile network provided by the LTE modem and antenna and exchanges data, sending work orders to the second microcomputer or requesting measurement or status data from the second microcomputer based on the received data.

The second microcomputer requests relay status data from the relay driver board via the serial communication protocol provided by the uart board or gives relay on/off orders.

The relay driver board executes orders to open and close peristaltic pumps and valves.

The pressure and temperature of the tank are continuously measured by a pressure and temperature sensor. The sampling period can be parametrically defined for each tank. (Example 15 minutes)

The second microcomputer receives the filling amount of the sample container, temperature data of the liquid in the tank and sample container, pH value of the liquid in the sample container, pressure data of the tank, calibration data of the pH sensor, float status data (full/empty data of the liquid containers). The sensor circuit receives temperature and pH data of the solution in the sample container and temperature data of the liquid in the tank. Other sensor data is calculated by the second microcomputer conversion method.

Sensor data is sent to the first microcomputer address in the Lora network formed by the Lora terminal and antenna.

The first microcomputer receives and analyzes data coming from the Lora terminal to its own address in the Lora network provided by the Lora Gateway and antenna.

Pressure Measurement

The pressure sensor reports the pressure in the tank to the second microcomputer, which transfers the information to the first microcomputer that processes it and sends it to the cloud. Then check whether the drain container is full.

Calculation of the Amount of Liquid in the Tank

When the tank is full and empty, the amount of liquid in the tank is calculated with a calibrated pressure sensor. The second microcomputer converts the liquid pressure into liquid level and then into volume information, which is reported to the first microcomputer and then processed and sent to the cloud. If there is no liquid in the tank, the system is put into standby mode until the situation changes.

Drain Container Process

The float informs the second microcomputer if the drain container is full or empty, and then the information is transmitted to the first microcomputer. The first microcomputer processes it and sends it to the cloud. If the drain container is full, the full information is sent to the cloud. The system is put into standby mode until the drain container is empty.

Manual draining process is started by opening the manual valve of the drain container. Since the draining process starts with the actuation of the peristaltic pump, the system is put into standby mode until the process is finished. When the drain container is empty, the draining process of the drain container is completed with the empty information coming from the drain float with the stop of the peristaltic pump. The manual valve is closed.

Solution Container Process

Check that the solution containers are full together with the drain container. The floats in the solution containers inform the second microcomputer that the containers are empty, which then transfers the information to the first microcomputer. The first microcomputer processes the information and sends it to the cloud. If the solution containers are empty, the system is put into standby mode until the containers are full.

Solution container filling is started with manual solution filling by opening the manual valve. Since the filling process starts with the actuation of the peristaltic pump, the system is put into standby mode until the process is finished. When the solution container is full, the filling process is completed with the full information from the filling float. The manual valve is closed. If the solution containers are not empty, the pressure in the tank is measured.

Tank Standby Process

When the tank is empty, the system is in standby mode and the sampling valve is closed. The pressure and temperature of the tank are continuously measured, waiting for the start of a process that will change the system state.

Tank Cleaning Process

If the tank pressure value is not within the empty state pressure range of the tank, the tank temperature is controlled by the temperature sensor. If the tank pressure value is within the pressure range of the tank cleaning status and the tank temperature is within the higher tank cleaning range, the tank cleaning process starts.

The amount of liquid in the sample container is checked. If there is liquid in the sample container, the liquid is transferred to the drain container by a peristaltic pump. If there is no liquid in the sample container or if the liquid has been drained, tank cleaning solution is taken from the tank to the sample container by a peristaltic pump. After cleaning the sample container, the cleaning solution is transferred to the drain container by a peristaltic pump. After the tank cleaning, the system is allowed to stand until the next measurement time.

Tank Filling Process

Measurement is made when the tank pressure goes beyond the full value range, the tank temperature is within the measurement value range and liquid can be drawn from the tank. Calibration values of the sensors are checked. If there is a deterioration in the calibration, the calibration process is started. If there is no deterioration, it is proceeded with sampling from the tank.

Calibration Process pH solution at pH 7.0 is transferred from the pH solution container to the sample container by a peristaltic pump. After the sensors have stable readings, calibration for pH 7.0 is performed. The calibration solution is then transferred to the drain container by a peristaltic pump. A peristaltic pump transfers the cleaning solution from the cleaning container into the sample container. The cleaning solution from the cleaned sample container is then transferred to the drain container by a peristaltic pump. After the cleaning process, pH solution at pH 4.0 is transferred from the pH solution container to the sample container by a peristaltic pump. After the sensors have stable readings, calibration for pH 4.0 is performed. The calibration solution is then transferred to the drain container by a peristaltic pump. A peristaltic pump transfers the cleaning solution from the cleaning container into the sample container. The cleaning solution from the cleaned sample container is transferred to the drain container by a peristaltic pump. Then, it is proceeded with sampling from the tank.

Sample Measurement Process

The sampling valve, which provides the connection between the tank and the measurement system, is only opened during the sampling process and is always closed in other cases. The measuring system is thus isolated from the tank. Sample is taken from the tank to the sample container by a peristaltic pump. The sampling valve is closed. Sample measurements are performed. The measured pH and temperature data are transferred from the second microcomputer to the first microcomputer via the Lora network. The first microcomputer processes the data it receives from the Lora network and sends it to the cloud via the mobile network. After the measurement process is finished, the system is allowed to stand until the next measurement time. (Example 15 minutes)

The first measurement is taken 2 to 3 minutes after the fluid level rises. Periodic measurement is then carried out.

Tank Draining Process

Draining of the tank starts with opening the tank drain valve. The tank drain float informs the second microcomputer that flow has occurred and the system is put into drain mode. Information is then transferred to the first microcomputer. The first microcomputer processes the information and sends it to the cloud. The system is taken out of drain mode when it is informed that the flow is cut off from the drain float and this information is sent to the cloud.

What is claimed is:

1. An in-tank raw milk monitoring system, characterized in that it includes a 12V transformer to create a direct current source for different units, a Long Range (LoRa) terminal, a Long Term Evolution (LTE) and a LoRa antenna to provide wireless long distance data exchange, a liquid level sensor to measure the amount of liquid coming into a sample container, a pressure sensor to measure the liquid pressure in a tank, a peristaltic pump to provide liquid flows, a manual valve for solution filling and draining, a Liquid Crystal Display (LCD) monitor for on-screen monitoring and management, a pH sensor for pH determination of milk, an LTE modem for mobile network connectivity, a first microcomputer for data processing and management, a second microcomputer for data acquisition and sensor management, a LoRa Gateway to collect wireless and long-distance sensor data, a voltage regulator to supply different voltage values to components, a temperature sensor to measure tank temperature, a relay board and a relay driver board to manage valves and pumps, a solenoid valve to connect the sample container to the tank, a solution box for sample and solution discharge, a Universal Asynchronous Receiver-Transmitter (UART) card for communication between the first microcomputer and the relay driver card, a float to measure the full and empty status of solution containers, an Uninterruptible Power Supply (UPS) to provide uninterrupted power to the system, and a sensor circuit to perform sensor data calculation and adjustment operations.

2. An in-tank raw milk monitoring method using an in-tank raw milk monitoring system that includes a 12V transformer to create a direct current source for different units, a Long Range (LoRa) terminal, a Long Term Evolution (LTE) and a LoRa antenna to provide wireless long distance data exchange, a liquid level sensor to measure the amount of liquid coming into a sample container, a pressure sensor to measure the liquid pressure in a tank, a peristaltic pump to provide liquid flows, a manual valve for solution filling and draining, a Liquid Crystal Display (LCD) monitor for on-screen monitoring and management, a pH sensor for pH determination of milk, an LTE modem for mobile network connectivity, a first microcomputer for data processing and management, a second microcomputer for data acquisition and sensor management, a LoRa Gateway to collect wireless and long-distance sensor data, a voltage regulator to supply different voltage values to components, a temperature sensor to measure tank temperature, a relay board and a relay driver board to manage valves and pumps, a solenoid valve to connect the sample container to the tank, a solution box for sample and solution discharge, a Universal Asynchronous Receiver-Transmitter (UART) card for communication between the first microcomputer and the relay driver card, a float to measure the full and empty status of solution containers, an Uninterruptible Power Supply (UPS) to provide uninterrupted power to the system, and a sensor circuit to perform sensor data calculation and adjustment operations, characterized in that the method includes process steps of:

connecting to a cloud and exchanging data by the first microcomputer with a mobile network provided by the LTE modem and the LoRa antenna, sending work orders to the second microcomputer or requesting measurement or status data from the second microcomputer based on data received from the cloud, requesting relay status data by the second microcomputer from the relay driver board via a serial communication protocol provided by the UART card, or issuing relay on/off orders, executing the relay on/off orders to open and close the peristaltic pump and valves by the relay driver board, measuring the pressure and temperature of the tank continuously by the pressure sensor and the temperature sensor and parametrically defining a sampling period for each tank, receiving data on the fullness of the sample container, temperature data of liquid in the tank and the sample container, a pH value of the liquid in the sample container, pressure data of the tank, calibration data of the pH sensor, float status data (full/empty data of liquid containers) by the second microcomputer, receiving the temperature and pH data of a solution in the sample container and the temperature data of the liquid in the tank by the sensor circuit, calculating other sensor data by the second microcomputer through a conversion method, and sending such sensor data to the first microcomputer address in a Long Range (LoRa) network formed by the LoRa terminal and the LoRa antenna, receiving and analyzing data by the first microcomputer from the LoRa terminal to its own address in the LoRa network provided by the LoRa Gateway and the LoRa antenna, as a part of the pressure measurement process, reporting the pressure in the tank by the pressure sensor to the second microcomputer, then transferring information to the first microcomputer, processing the information and sending the information to the cloud, then checking whether a drain container is full or not, p1 as a part of calculating the amount of liquid in the tank, calculating the amount of liquid in the tank with a calibrated pressure sensor when the tank is full and empty, converting the liquid pressure into liquid level and then into volume information by the second microcomputer and reporting this information to the first microcomputer, then processing the information and sending it to the cloud, if there is no liquid in the tank, putting the system into standby mode until the situation changes, as a part of the drain container process, informing the second microcomputer by the float when the drain container is full or empty, and then transferring information to the first microcomputer, processing the information and sending it to the cloud by the first microcomputer, sending full information to the cloud if the drain container is full, putting the system in standby mode until the drain container is empty, starting manual draining process by opening a manual valve of the drain container, since the draining process starts with the actuation of the peristaltic pump, putting the system into standby mode until the process is finished, when the drain container is empty, stopping the peristaltic pump and draining the drain container based on the empty information from a drain float and closing the manual valve, as a part of the solution container process, checking that solution containers are full together with the drain container, informing the second microcomputer that the containers are empty by floats in the solution containers, then transferring the information to the first microcomputer, processing the information and sending it to the cloud by the first microcomputer, if the solution containers are empty, putting the system into standby mode until the containers are filled, starting solution container filling with the opening of the manual valve, since the filling process starts with the actuation of the peristaltic pump, putting the system into standby mode until the process is finished, when the solution container is full, completing the filling process with the full information from a filling float and closing the manual valve, if the solution containers are not empty, starting the pressure measurement in the tank, as a part of the tank standby process, keeping the system in standby mode and a sample valve in the closed position when the tank is empty, continuously measuring the pressure and temperature of the tank and waiting for the start of a process that will change the system state, as a part of the tank cleaning process, checking the tank temperature with the temperature sensor if the tank pressure value is not in the empty state pressure range of the tank, starting the tank cleaning process if the tank pressure value is in the cleaning state pressure range of the tank and the tank temperature is in the higher tank cleaning range, checking the amount of liquid in the sample container, if there is liquid in the sample container, transferring the liquid to the drain container by the peristaltic pump, if there is no liquid in the sample container or if the liquid has been drained, taking the tank cleaning solution from the tank to the sample container by the peristaltic pump, after the sample container is cleaned, transferring the cleaning solution to the drain container by the peristaltic pump, after the tank cleaning is finished, allowing the system to stand until the next measurement time, as a part of the tank filling process, measuring if the tank pressure goes beyond the full value range, the tank temperature is within the measurement value range and liquid can be drawn from the tank, checking the calibration values of the sensors, starting the calibration process if there is a deterioration in the calibration, and if there is no deterioration, proceeding with the sampling process from the tank, as a part of the calibration process, transferring the solution at pH 7.0 from a pH 7.0 solution container to the sample container by the peristaltic pump, performing calibration for pH 7.0 after the sensors make a stable reading, then transferring the calibration solution to the drain container with the peristaltic pump, transferring the cleaning solution from a cleaning container to the sample container by the peristaltic pump, then transferring the cleaning solution in the cleaned sample container to the drain container by the peristaltic pump, transferring the pH solution from a pH 4.0 solution container to the sample container by the peristaltic pump after cleaning, performing pH 4.0 calibration after the sensors have stable readings, then transferring the calibration solution to the drain container by the peristaltic pump, transferring the cleaning solution from the cleaning container to the sample container by the peristaltic pump, transferring the cleaning solution in the cleaned sample container to the drain container by the peristaltic pump, then proceeding to the sampling process from the tank, as a part of the sample measurement process, opening a sample valve connecting the tank to the measurement system only during the sampling process and always closing it in other cases, taking samples from the tank to the sample container by the peristaltic pump, closing the sample valve and taking sample measurements, taking the first measurement 2 to 3 minutes after the liquid level rises, then making the periodic measurements, transferring the measured pH and temperature data from the second microcomputer to the first microcomputer via the LoRa network, processing the data received from the LoRa network and sending it to the cloud via the mobile network by the first microcomputer, after the measurement process is over, allowing the system to stand until the next measurement time, and as a part of the tank draining process, starting the drainage of the tank with the opening of a tank drain valve, informing the second microcomputer by a tank drain float that flow has occurred and putting the system into drain mode, then transferring information to the first microcomputer, processing the information and sending it to the cloud by the first microcomputer, removing the system from the drain mode when the information that the flow has stopped is received from the drain float and sending this information to the cloud.

* * * * *